United States Patent [19]

Golias

[11] Patent Number: 5,137,614

[45] Date of Patent: Aug. 11, 1992

[54] IMMUNOFIXATION ELECTROPHORESIS CONTROL SYSTEM

[75] Inventor: Tipton L. Golias, Beaumont, Tex.

[73] Assignee: Helena Laboratories Corporation, Beaumont, Tex.

[21] Appl. No.: 231,032

[22] Filed: Aug. 11, 1988

[51] Int. Cl.[5] .................. G01N 27/26; G01N 33/561; B01D 57/02

[52] U.S. Cl. ...................... 204/199 R; 204/182.8; 204/180.1; 436/516

[58] Field of Search .............. 204/299 R, 182.8; 436/516

[56] References Cited

U.S. PATENT DOCUMENTS

| | | | |
|---|---|---|---|
| 4,018,662 | 4/1977 | Ruhenstroth-Bauer | 204/299 R |
| 4,207,166 | 6/1980 | Dahms | 204/299 R |
| 4,668,363 | 5/1987 | Gebott | 204/182.8 |

FOREIGN PATENT DOCUMENTS 0280570  12/1986  Japan .................. 436/516

Primary Examiner—John F. Niebling
Assistant Examiner—John S. Starsiak, Jr.
Attorney, Agent, or Firm—Spencer & Frank

[57] ABSTRACT

An improvement in the immunofixation electrophoresis procedure for detecting proteins in serum, urine or cerebral spinal fluids. Samples are placed on a gel and subjected to electrophoresis for resolving or separating proteins. Thereafter, antisera are applied to the sample areas to cause an antibody-antigen precipitation reaction if the specific proteins are present. The invention includes the provision of a control system for each electrophoretic gel to verify that the antisera have retained their lability, i.e., the ability to react.

42 Claims, 1 Drawing Sheet

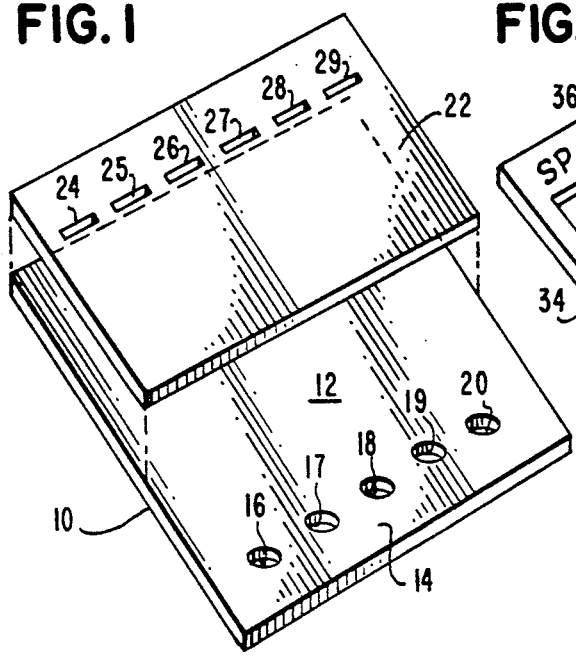
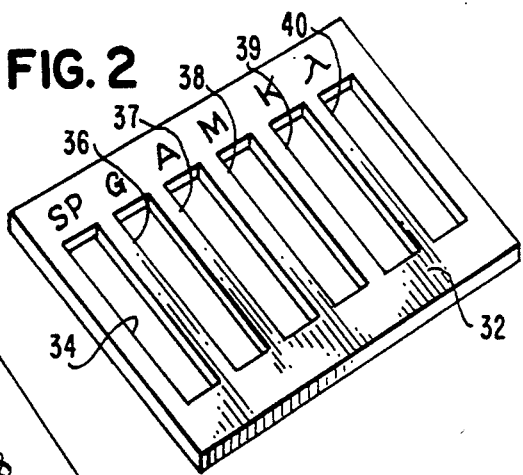
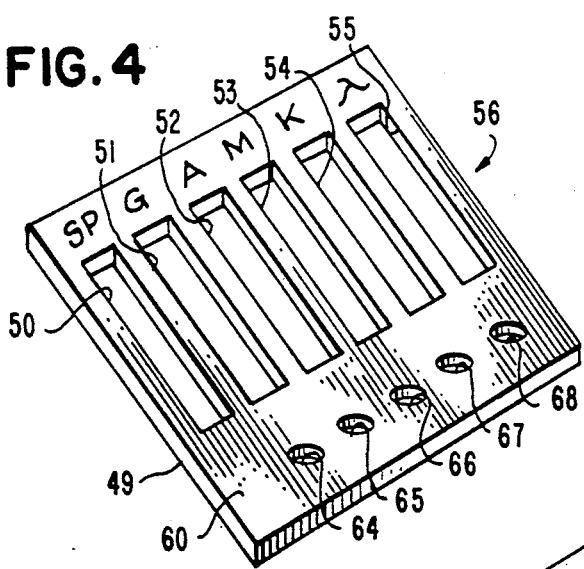
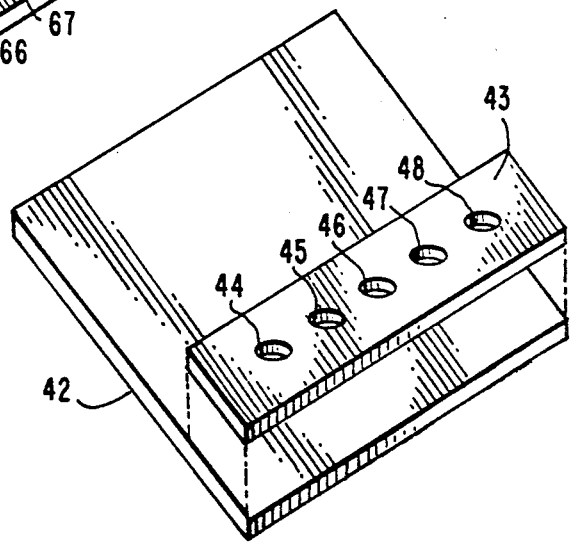

IMMUNOFIXATION ELECTROPHORESIS CONTROL SYSTEM

BACKGROUND OF THE INVENTION

The present invention relates to immunofixation electrophoresis procedures in general and, in particular, to an improved control system for verifying the effectiveness of the chemicals utilized in the immunofixation electrophoresis procedure.

DESCRIPTION OF THE PRIOR ART

Immunofixation electrophoresis, known as IFE, is well-known as a two-stage procedure for detecting the presence of certain proteins in human serum, urine or cerebral spinal fluid. The procedure involves, as a first step, protein fraction resolution by electrophoresis. As a second step, the soluble antigen in the protein is allowed to react with its antibody (antiserum). The resultant antigen-antibody complexes will precipitate, at a rate dependent upon the proportion of the reactants, temperature, salt concentration and pH. The antigen-antibody complexes are then visualized by staining.

The IFE process is described, in greater detail in Gebott et al, U.S. Pat. No. 4,668,363 issued May 26, 1987, and of course, in the bibliography listed at column 4 of that patent. Apparatus and chemicals for performing IFE have been marketed for some time by Helena Laboratories Corporation of Beaumont, Tex.

Typically, a specimen from a single patient is diluted and then placed in multiple sample or application areas on a single electrophoretic gel plate. The purpose of utilizing multiple sample areas is to enable detection, separately, of total serum protein, various proteins such as the immunoglobin heavy chains IgG, IgM, IgA and light chains Kappa and Lambda, or other proteins whose presence or absence may be of importance in medical diagnosis.

Prior to the present invention, in order to determine the effectiveness of the chemicals, i.e., the antisera, and even the protein fixative and the stain, a technique known as batch control testing was employed. Batch control testing refers to the use, on a single electrophoretic gel plate, of known sera and known antisera to force the sera-antisera precipitation reactions. In this manner, the proper functioning of all the antisera could be verified.

There are, of course, potential drawbacks with batch control testing, such as failure to take into account the fact that chemicals may lose their effectiveness at any time. Hence, chemicals which are effective at the beginning of the day, when a batch control test is performed, may lose their effectiveness later in the day. The ability of the chemicals such as the antisera to react with the sera is generally referred to as lability.

Equally, when utilizing batch control testing, each time a particular antiserum must be replenished, the IFE specimen testing must be interrupted for the purpose of a new control test of the proper functioning of the antiserum. Another problem which was undetected by batch control testing was that the laboratory technician might apply antisera to the incorrect sample area, as will be explained in greater detail.

SUMMARY OF THE INVENTION

The present invention overcomes the difficulties and shortcomings of batch controls in immunofixation electrophoresis by providing a control system permitting controls on each and every electrophoresis gel plate which do not interfere with the protein detection, do not cause the delay which is inherent in IFE specimen testing if a gel plate is utilized solely as a control plate, as has been previously done, and consequently reduces wasted agarose gel plates which heretofore had to be used either for controls or for patient samples, but not both, in the IFE procedure. The present invention also avoids the need to interrupt patient specimen evaluation when chemicals, e.g., antisera, are replenished, since the very chemicals utilized on the specimens are also utilized in the control test. Also, the present invention may be employed to verify that the antisera are being placed in the proper sample areas.

BRIEF DESCRIPTION OF THE DRAWINGS

The various objects, advantages and benefits of the present invention will become more apparent upon reading the following detailed description of the invention taken in conjunction with the drawings.

In the drawings, where like reference numerals identify corresponding elements:

FIG. 1 is a perspective exploded diagrammatic illustration of an electrophoresis gel plate and a template for application of the patient sample to the gel plate in accordance with the principles of the present invention;

FIG. 2 is a perspective illustration of a template for application of the antisera to the gel plate in accordance with the principles of the present invention;

FIG. 3 is a perspective exploded illustration of a variation in the agarose gel plate and the template according to the principles of the present invention; and FIG. 4 is a perspective illustration of yet another variation in the template according to the principles of the present invention.

DETAILED DESCRIPTION OF THE INVENTION

With reference to the drawings, an electrophoresis plate, such as an agarose gel plate 10 is illustrated in FIG. 1. The gel plate is illustrated in diagrammatic form and includes a first area 12 for application of the sample from the patient, and a control area 14. For the purposes of explanation of this invention in the context of an IFE control system, the control area 14 is illustrated as including five discrete control regions such as wells or depressions, 16, 17, 18, 19, and 20, in the surface of the gel. Aligned (diagrammatically) above the gel plate 10 is a first template 22. Template 22 includes six slits, 24, 25, 26, 27, 28 and 29, aligned across the template 22 and when the template is placed over the gel plate and patient samples introduced into the slits, the patient samples will be deposited on the first area 12 of the gel plate. All of this description relative to the gel plate and the template 22, excluding the provision of the control area 14 and wells 16-20, respectively, is old and well-known, and is conventional for the electrophoresis aspect of IFE.

It should be appreciated that the use of five wells and six slits is merely representative when five proteins (and total serum protein) are to be investigated. Additional wells (and slits) should be provided when testing is for more than five proteins. For ease of explanation, only five wells and six slits are illustrated.

FIG. 2 illustrates a second template 32 having multiple elongated, aligned slots therethrough. Template 32 may be considered as an antisera application template.

The first elongated slot 34, as is conventional with IFE, is for analysis of total serum protein (SP) and the five remaining slots, 36, 37, 38, 39, and 40 will each ultimately be utilized in the detection of a different protein. Again, this is conventional with six channel IFE.

The method of the present invention, and thus the method of IFE controls for each electrophoresis plate will now be explained. With respect to the electrophoresis step, as is conventional, the specimen is divided into multiple diluted portions and placed in slits 24-29, respectively of template 22, to thus be properly positioned in the specimen test area 12 on the agarose gel plate.

After the specimen is thus placed in the aligned areas on the agarose gel plate, the agarose gel plate is subjected to electrophoresis as is conventional. This completes the electrophoresis portion of the instant invention.

Proceeding next to the immunofixation portion of the present invention, the template 32 is placed on the electrophoreses gel.

The multiple elongated slots 34 and 36-40 are aligned over the electrophoresed samples. It should be noted that the length of the template 32 is such that the wells 16-20 in the gel plate are not covered.

Then, according to the method of the present invention, control solutions may be introduced into each of the wells in the control application area.

The controls are prepared from human sera and, as part of the preferred embodiment of the present invention, only three distinct control solutions are required for the five control areas when testing for the five proteins previously identified. However, depending upon the specific proteins which are to be detected in the patient samples, plus the number of proteins separated out on a single gel plate (e.g., five, ten, twenty, thirty, etc.) the number of distinct control solutions will vary.

The sample areas where protein fractions are separated are frequently called channels. Thus in the drawings, the illustrated example may be thought of as a six channel system. Six channels, while common in IFE, is not a limitation either on the IFE procedure or in the utility of the present invention.

In the illustrated example, the six sample areas or channels are designated SP, for total serum protein, G, A, M, K, and L. These last five designations are used because in the illustrated example of the IFE procedure, the presence or absence of the monoclonal immunoglobins IgG, IgA, IgM, Kappa, and Lambda are to be determined.

The first control solution has been prepared from human sera containing an IgG Kappa monoclonal protein and this is applied to the G and Kappa control wells 16 and 19, respectively. A second control solution prepared from human sera containing the IgA Lambda monoclonal protein is applied to the A and Lambda control wells 17 and 20, respectively. The third control, prepared from human sera containing IgM monoclonal protein, is applied to the M control well 18.

Next, returning the conventional aspects of the immunofixation portion of the procedure, with template 32 still on the gel plate, protein fixative is applied through the slot 34 and this will provide the complete electrophoresis pattern upon completion of staining. Antiserum IgG is applied through slot 36 and placed in well 16, antiserum IgA is applied through slot 37 and placed in well 17, antiserum IgM is applied through slot 38 and placed in well 18, antiserum to human serum Kappa light chain is applied through slot 39 and placed in well 19, and antiserum to human Lambda light chain is applied through slot 40 and placed in well 20. The sample is then incubated, the template 32 removed, and the agarose gel plate is subjected to the standard washing, drying and staining.

If each of the chemicals (sera and antisera) is labile and thus functioning properly, there will be precipitin rings on the gel plate at each of the wells 16-20 which indicates reactive antisera and reactive monoclonal sera. One additional benefit of control testing on each gel plate is to verify that each antiserum has been placed in the proper channel or slot and corresponding well. It is a potential problem that a laboratory technician might place antiserum in the wrong slot and this potential problem may be increased in a twenty or thirty channel plate. Placing antiserum in the slot and in the corresponding well as part of the built-in control system of this invention provides for detection (by non-reaction with the serum) of antiserum being placed in the inappropriate slot.

It should be further appreciated that according to the principles of the present invention it is not necessary that all sample areas be utilized on a single electrophoresis plate. Hence it is within the scope of the present invention to use an electrophoresis plate and the IFE procedure to test for only a single monoclonal protein.

Referring next to FIG. 3, an alternate form of gel plate 42 and template 43 are illustrated. Gel plate 42 does not contain wells or depressions for application of the control system of the present invention. Rather, template 43 includes a plurality of apertures 44, 45, 46, 47 and 48 therethrough. Template 43 may be used in conjunction with template 32 of FIG. 2 in that the reactive human sera (i.e., the control solutions) and the antisera may be applied through the apertures to verify the lability of the antisera and sera. Of course each antiserum should be applied through its respective slot in template 32 and its aperture in template 43 (in sequence) to maintain the advantage of detecting if an antiserum was placed in the wrong slot as previously described. Template 43 may be considered a control area template.

Referring now to FIG. 4, yet another form of template 49 is illustrated. Template 49 may be thought of as a combination of templates 32 and 43. As such, template 49 may be utilized with an electrophoretic gel plate which does not include wells in the control area. Template 49 thus includes a specimen application area, namely elongated slots 50-55 therethrough corresponding to the slots 34 and 36-40 in the template of FIG. 2. This "specimen" application area, generally designated 56, and corresponding to template 32, is for the application of antisera over the electrophoresed samples. Template 49 also includes a control area 60, corresponding in its entirety to template 43. Control area 60 is illustrated for the purpose of explanation, as having five apertures 64-68 therethrough, each aligned below a respective slot 51-55. When a template 49 as illustrated in FIG. 4 is utilized, slots 50-55 are aligned over the electrophoresed samples and apertures 64-68 will facilitate placement of sera and antisera in the control area, and will retain the benefit of placement of antisera on the electrophoresed samples.

Many changes and modifications may be made without departing from the spirit and scope of the present invention. The present invention, therefore, should be limited only by the following claims.

What is claimed:

1. In a method for immunofixation electrophoresis where at least one sample is applied to at least one application area on an electrophoretic gel, the sample is thereafter electrophoresed to obtain an electrophoresis protein separation pattern of the sample, an antiserum capable of reacting with a protein is applied to the application area on said electrophoresed sample, and said electrophoresed sample with the antiserum applied is to be incubated, the improvement comprising:

defining a control area on said electrophoretic gel for verifying the lability of antisera, said control area associated with but discrete from said application area;

applying control serum to said control area;

applying antiserum to the same control area, said control serum and antiserum being in contact with each other at the same control area, and thereafter incubating said gel;

said control serum and said anitserum for providing an antibody-antigen reaction if the control serum and antiserum have retained their lability.

2. The method as defined in claim 1 wherein the sample is applied in multiple application areas and where multiple, discrete control sites are provided at the control area of said electrophoresed sample.

3. The method as defined in claim 2 wherein control serum is applied to each of said control sites and antiserum is applied to each of said control sites prior to said step of incubating.

4. The method of claim 3 wherein the control serum applied to at least one of said control sites contains the IgM monoclonal protein.

5. The method as defined in claim 3 wherein the control serum applied to at least two of the control sites contains the IgG Kappa monoclonal protein.

6. The method as defined in claim 3 wherein the control serum applied to at least two of said control sites contains the IgA Lambda monoclonal protein.

7. The method as defined in claim 2 wherein different antisera are applied to individual control sites.

8. The method as defined in claim 7 wherein each of said different antisera is sequentially applied to said application area and said associated control area.

9. The method as defined in claim 1 wherein recesses are provided in said control area, of said gel.

10. The method as defined in claim 1 wherein at least one of the control serum and said antiserum are applied through a template.

11. In a system for immunofixation electrophoresis where a sample is applied to at least one application area on an electrophoretic gel, the sample is thereafter electrophoresed to obtain electrophoretic protein separation of the sample, and an antiserum capable of reacting with a protein is applied to said electrophoresed sample and is thereafter to be incubated, said system including a first template having at least one slot therethrough associated with said at least one application area on said electrophoretic gel for the introduction of said antiserum through said slot onto said electrophoretic gel, the improvement comprising:

a template means having at least one control aperture extending therethrough, said control aperture discrete from but associated with said application slot;

said control aperture for the application of both control serum and antiserum onto said electrophoretic gel, in contact with each other prior to incubation for verifying that the control serum and antiserum have retained their lability.

12. The invention as defined in claim 11 wherein said first template has at least five sample application areas therethrough for application of multiple antisera onto said gel and said template means includes at least five control apertures therethrough, each control aperture discrete from and associated with one of said sample application areas, each of said control apertures for the application of both control sera and antisera onto said gel.

13. The invention as defined in claim 12 wherein different antisera are applied through each control aperture.

14. The invention as defined in claim 11 wherein said template means is distinct from the first template associated with said at least one application area.

15. The invention as defined in claim 11 wherein said template means is integrally formed with the first template associated with said at least one application area.

16. The invention as defined in claim 1 wherein the sample is applied to the electrophoretic gel through a template.

17. The invention as defined in claim 1 wherein the antiserum for the application area is applied through a template.

18. The invention as defined in claim 1 wherein the control serum is applied through a template.

19. The invention as defined in claim 1 wherein the antiserum for the control area is applied through a template.

20. The invention as defined in claim 19 wherein the control serum and the antiserum for the control area are each applied through the same template.

21. The invention as defined in claim 1 wherein the control serum has a known monoclonal gammopathy.

22. The invention as defined in claim 1 wherein a plurality of control sera are provided, each having a known monoclonal gammopathy.

23. The invention as defined in claim 11 wherein said system further includes a second template having at least one slit therein associated with said at least one application area on said electrophoretic gel for the application of a sample to the electrophoretic gel.

24. The invention as defined in claim 11 wherein the control serum has a known monoclonal gammopathy.

25. The invention as defined in claim 11 wherein a plurality of control sera are provided, each having a known monoclonal gammopathy.

26. The invention as defined in claim 11 wherein the antiserum includes at least one antiserum selected from the group consisting of antiserum to human IgG, antiserum to human IgA, antiserum to human IgM, antiserum to human lambda light chain, and antiserum to human kappa light chain.

27. In a system for immunofixation electrophoresis where a sample is applied to at least one application area on an electrophoretic gel, the sample is thereafter electrophoresed to obtain electrophoretic protein separation of the sample, and at least one antiserum capable of reacting with a protein is applied to said gel and is thereafter to be incubated, the improvement comprising:

control means discrete from but associated with said application area for verifying the lability of at least one antiserum;

said control means for the application of at least one control serum and at least one antiserum onto said gel, in contact with each other, prior to incubation, for verifying that the at least one control serum and the at least one antiserum have retained their lability.

28. The invention as defined in claim 27 wherein said control means is at least one well in said electrophoretic gel.

29. The invention as defined in claim 27 wherein said control means is a template having at least one aperture therethrough.

30. A kit for immunofixation electrophoresis of a sample, wherein a sample is electrophoresed, antiserum is thereafter applied to the electrophoresed sample, and thereafter the electrophoresed sample containing antiserum is incubated, comprising, as components, at least one antiserum, at least one control serum, and control means for maintaining said at least one antiserum and said at least one control serum in contact during incubation.

31. The invention as defined in claim 30 wherein said at least one antiserum is selected from the group consisting of antiserum to human IgG, antiserum to human IgA, antiserum to human IgM, antiserum to human lambda light chain, and antiserum to human kappa light chain.

32. The invention as defined in claim 30 wherein said at least one control serum has a known monoclonal gammopathy.

33. The invention as defined in claim 30 wherein the kit further includes a protein fixative.

34. The invention as defined in claim 30 wherein the kit further includes a stain.

35. The invention as defined in claim 30 wherein the kit further includes an electrophoretic gel.

36. The invention as defined in claim 30 wherein the kit further includes an agarose electrophoretic gel.

37. The invention as defined in claim 30 wherein the kit further includes an electrophoretic gel and at least one template for the application of the sample to the electrophoretic gel.

38. The invention as defined in claim 30 wherein the kit further includes at least one template for the application of the at least one antiserum to the electrophoresed sample.

39. The invention as defined in claim 30 wherein the control means is a template having apertures therethrough.

40. The method as defined in claim 1 wherein said at least one sample is provided by a single patient.

41. The method as defined in claim 2 wherein said sample is provided by a single patient.

42. The invention as defined in claim 11 wherein said sample is provided by a single patient.

* * * * *